(12) United States Patent
Kato

(10) Patent No.: US 11,701,336 B2
(45) Date of Patent: Jul. 18, 2023

(54) METHOD OF DETERMINING COMPOSITION EFFECTIVE FOR TREATING DIABETES

(71) Applicant: Yasumasa Kato, Yokohama (JP)

(72) Inventor: Yasumasa Kato, Yokohama (JP)

( * ) Notice: Subject to any disclaimer, the term of this patent is extended or adjusted under 35 U.S.C. 154(b) by 6 days.

(21) Appl. No.: 17/063,673

(22) Filed: Oct. 5, 2020

(65) Prior Publication Data

US 2021/0093600 A1  Apr. 1, 2021

Related U.S. Application Data

(63) Continuation-in-part of application No. 15/939,289, filed on Mar. 29, 2018, now abandoned, which is a continuation of application No. PCT/JP2016/082066, filed on Oct. 28, 2016.

(30) Foreign Application Priority Data

Oct. 30, 2015 (JP) .............................. JP2015-214824

(51) Int. Cl.

| | |
|---|---|
| *G01N 33/53* | (2006.01) |
| *A61K 31/198* | (2006.01) |
| *A61K 31/522* | (2006.01) |
| *A61K 31/40* | (2006.01) |
| *A61K 31/4985* | (2006.01) |
| *A61K 31/496* | (2006.01) |
| *A61K 31/155* | (2006.01) |
| *G01N 33/72* | (2006.01) |
| *G01N 33/50* | (2006.01) |
| *A61P 3/10* | (2006.01) |
| *A61K 31/506* | (2006.01) |

(52) U.S. Cl.
CPC .......... *A61K 31/198* (2013.01); *A61K 31/155* (2013.01); *A61K 31/40* (2013.01); *A61K 31/496* (2013.01); *A61K 31/4985* (2013.01); *A61K 31/506* (2013.01); *A61K 31/522* (2013.01); *A61P 3/10* (2018.01); *G01N 33/5088* (2013.01); *G01N 33/723* (2013.01); *G01N 2800/042* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2004/0063780 | A1 | 4/2004 | Matsuoka et al. |
| 2005/0124693 | A1* | 6/2005 | Taka .................... A61P 1/16 514/471 |
| 2006/0205633 | A1 | 9/2006 | Nishitani et al. |
| 2013/0017283 | A1 | 1/2013 | Zemel et al. |

FOREIGN PATENT DOCUMENTS

| | | |
|---|---|---|
| JP | 2004-002272 A | 1/2004 |
| JP | 2007-008814 A | 1/2007 |
| WO | 2005/049006 A | 6/2005 |
| WO | 2011/051974 A | 5/2011 |
| WO | 2013/134736 A | 9/2013 |
| WO | 2016/049236 A | 3/2016 |

OTHER PUBLICATIONS

Salpeter et al., Risk of Fatal and Nonfatal Lactic Acidosis with Metformin use in Tpe 2 Diabetes Mellitus, Arch Intern Med, vol. 163, Nov. 24, 2003, pp. 2594-2602. (Year: 2003).*
Matsumoto et al ., Branched-Chain Amino Acid Supplementation Increases the Lactate Threshold during and Incremental Exercise Test in Trained Individuals, J Nutr Sci Vitaminol, 55, 2009, pp. 52-58. (Year: 2009).*
Lizhi Fu et al., Interaction between metformin and leucine in reducing hyperlipidemia and hepatic lipid accumulation in diet-induced obese mice, Metabolism, Jul. 17, 2015, vol. 64, No. 11, pp. 1426-1434.
International Search Report for PCT/JP2016/082066 dated Nov. 22, 2016, English portions only.
PCT written opinion dated Nov. 22, 2016.
Japanese notice of the reason for refusal dated Oct. 17, 2017, English portions only.
Japanese decision to grant a patent dated Nov. 14, 2017, English portions only.
Extended European Search Report dated Oct. 4, 2018.
James Heaf: "Metformin in Chronic Kidney Disease: Time for a Rethink", Peritoneal Dialysis International, vol. 34, pp. 353-357, Jun. 1, 2014.
Sarah Vecchio, et al: "Metformin-induced lactic acidosis: no one left behind", Critical Care, vol. 15, No. 1, pp. 107-108, Jan. 1, 2011.

* cited by examiner

*Primary Examiner* — Gary Counts
(74) *Attorney, Agent, or Firm* — Yokoi & Co., U.S.A.; Toshiyuki Yokoi

(57) ABSTRACT

The treatment of diabetes mellitus with excellent hypoglycemic effect that suppresses lactic acidosis without substantially increasing the blood lactate concentration. A composition for treating diabetes mellitus with hypoglycemic effect that suppresses lactic acidosis without substantially increasing the blood lactate concentration, and the composition has branched-chain amino acids and salts of biguanide derivatives and derivatives of biguanide derivatives or branched-chain amino acids as the active components. The composition will be more effective when leucine, isoleucine, or valine is included as branched-chain amino acids, and metformin as the biguanide derivative.

6 Claims, 4 Drawing Sheets

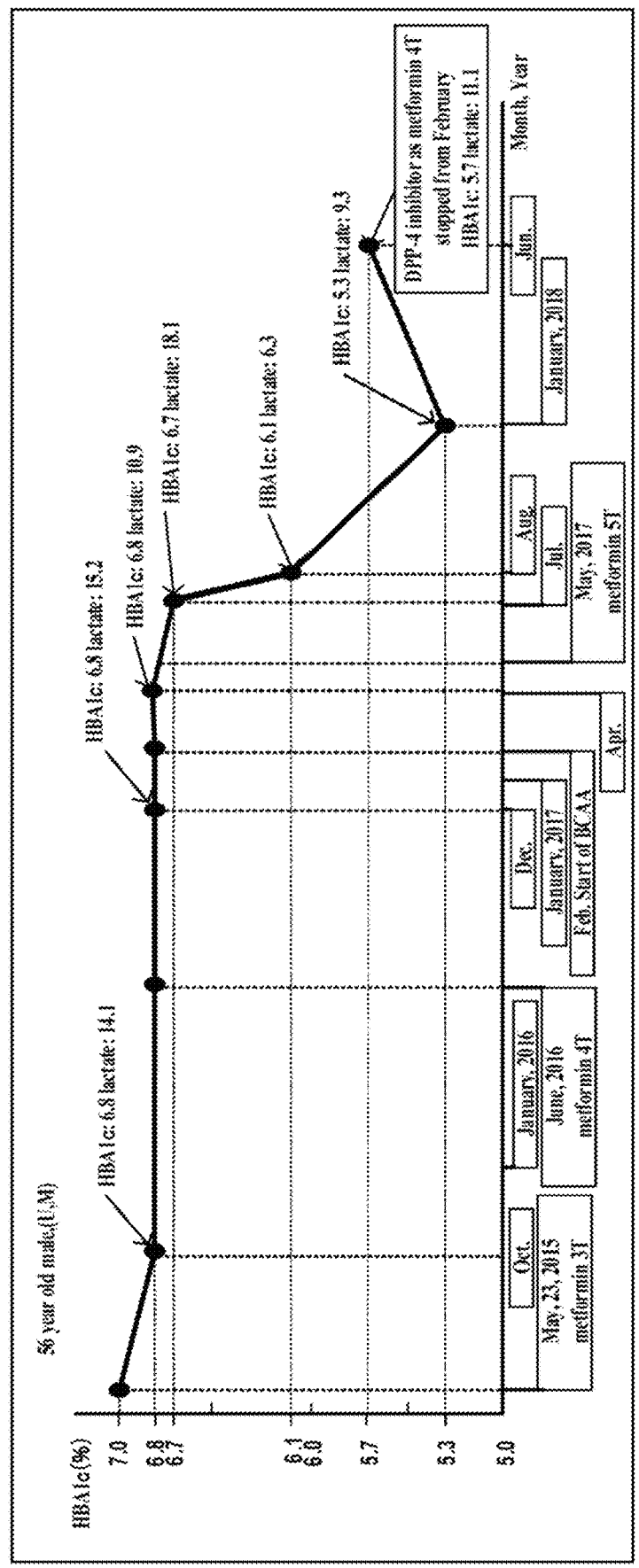

Fig. 2

*Treatment of diabetes mellitus was first started on 2000 (38 year old). HBA1c: 7.9

*HBA1c was decreased once but increased again. Thus, Metformin was started to be used from May, 2015.

*BCAA has an effect of reducing lactate. Thus, it seems that BCAA enhances the effect of Metformin.

*The value of lactate was increased to 18.1 just after Metformin is 5T is applied. However, the value immediately decreased to 6.3.

82 years old, male

METHOD OF DETERMINING COMPOSITION EFFECTIVE FOR TREATING DIABETES

CROSS-REFERENCES TO RELATED APPLICATIONS

This application is a Continuation-In-Part application claiming the benefit of priority of the co-pending U.S. Utility Non-Provisional patent application Ser. No. 15/939,289, with a filing date of Mar. 29, 2018, the entire disclosures of all applications are expressly incorporated by reference in their entirety herein.

BACKGROUND OF THE INVENTION

1. Field of the Invention

The present invention relates to a therapeutic agent for treating diabetes, more specifically, a therapeutic agent for diabetes mellitus with biguanide derivative such as metformin, and branched-chain amino acids such as valine, leucine, and isoleucine as the active components.

2. Description of Related Art

Hypoglycemic agents are one of the conventional treatments used for diabetic patients. Oral hypoglycemic agents such as insulin preparation, sulfonylurea drugs, thiazolidinedione derivatives, alpha-glucosidase inhibitors, and biguanide agents are mainly used (for example, Patent Document 1).

[Patent document 1] Japanese Unexamined Patent Application Publication No. 2007-008814

BRIEF SUMMARY OF THE INVENTION

Among oral hypoglycemic agents, the possibility of biguanide derivatives causing lactic acidosis is recognized to be high. For example, existing biguanide agents such as metformin are associated with the risk of causing lactic acidosis among diabetic patients with a history of lactic acidosis, diabetic patients with renal dysfunction, diabetic patients with liver dysfunction, diabetic patients with cardiovascular disorders, diabetic patients with impaired pulmonary function, diabetic patients who are prone to hypoxemia, diabetic patients who consume excess alcohol, diabetic patients with gastrointestinal disorders, and elderly diabetic patients.

The present invention intends to solve the above problem by providing a composition for treating diabetes mellitus having excellent hypoglycemic effect that suppresses lactic acidosis without substantially increasing the blood lactate concentration.

To achieve the above objective, the present invention provides a composition for treating diabetes mellitus with hypoglycemic effect that suppresses lactic acidosis without substantially increasing the blood lactate concentration, and is characterized by a branched-chain amino acid or a derivative of a branched-chain amino acid, and biguanide derivative or a salt of the biguanide derivative as the active component. And this composition can be used for the analysis of diabetes.

And the present invention provides a diabetes analysis method comprising:

a step to measure HbA1c and lactate levels in a patient and detect tumor markers in the patient, a step of blending a composition containing a branched chain amino acid, a biguanide derivative and an antidiabetic agent as active ingredients according to the measurement results of HbA1c and lactic acid levels, a step of measuring changes in HbA1c, lactate levels and tumor markers after administration of the composition to the patient, a step of repeating administration while adjusting the composition of the composition according to the measurement result after administration, and a step of observing the correlation between the process until the HbA1c or lactic acid level reaches the reference value and the formulation of the composition at each administration.

The composition for treating diabetes mellitus of the present invention may contain either leucine, isoleucine, or valine, or both leucine and isoleucine, or, all of leucine, isoleucine, and valine as the branched-chain amino acid.

The composition for treating diabetes mellitus of the present invention may contain metformin, phenformin, or buformin as the biguanide derivative.

The disease to be treated by the composition for treating diabetes mellitus of the present invention can be selected from at least one among the groups of, diabetes mellitus associated with a history of lactic acidosis, diabetes mellitus associated with renal dysfunction, diabetes mellitus associated with liver dysfunction, diabetes mellitus associated with cardiovascular disorders, diabetes mellitus associated with impaired pulmonary function, diabetes mellitus that can easily accompany hypoxemia, diabetes mellitus in persons who consume excess alcohol, diabetes mellitus associated with gastrointestinal disorders, type 2 diabetes, and diabetes mellitus in older adults.

The other target disease of the present invention can be diabetes mellitus associated with renal dysfunction and the invention can also be used for the prevention and treatment of lactic acidosis.

The present invention can be in the form of infusion or oral preparations.

The composition of the present invention described above is also effective as an agent for treatment, prevention and improving diseases and symptoms mediated by DPP4.

1. Supplementation and enhancement of the treatment and preventive effectiveness of the composition, 2. Improvement of the dynamics and absorption of the composition, reduction in dosage, and 3. May be administered as a drug combined with other drugs to alleviate side effects caused by the composition.

For example, can be administered as a drug in combination with Branched-Chain Amino Acids (BCAA), biguanide derivatives such as metformin or salts of the biguanide derivatives and derivatives of branched-chain amino acids or therapeutic agents used in the treatment of diabetes mellitus.

The above-mentioned therapeutic agents used in the treatment of diabetes mellitus include but are not limited to dipeptidyl peptidase-4 inhibitors (hereinafter abbreviated as "DPP4 inhibitors"), sulfonylurea hypoglycemic drugs, biguanide preparations, α-glucosidase inhibitors, rapid-acting insulin secretagogues, insulin preparations, PPAR agonists, (33 adrenergic receptor agonists, aldose reductase inhibitors, GLP-1 analogs, and SGLT inhibitors.

DPP4 inhibitors include vildagliptin, P-32/98, P-93/01, TS-021, 815541, 825964, denagliptin, TA-6666, MK-0431/ONO-5435, SYR-322, SK-042, saxagliptin, and KRP-104.

The drug containing the composition of the present invention may be administered as a combination drug in which all the components are combined in one formulation or administered in the form of separate formulations. Administration as separate formulations includes simultaneous and separate administrations. Also, when administering separately, the compound of the present invention may be administered first, and the other drug may be administered later, or the other drug may be administered first, and the compound of the present invention may be administered later, and respective mode of administration may be the same or different.

As described above, according to the composition for treating diabetes mellitus of the present invention, a therapeutic agent with excellent hypoglycemic effect that suppresses lactic acidosis without substantially increasing the blood lactate concentration is provided.

The composition of the present invention is also effective as an agent for treating, preventing and improving diseases and symptoms mediated by DPP4, and can also be used in combination with common therapeutic agents used in the treatment of diabetes mellitus. DPP4 inhibitors are present in new drugs of diabetes mellitus and use of drugs formulated by combining DPP4 inhibitors and metformin has started recently, and there is widespread recognition that blood glucose cannot be controlled without using a biguanide derivative like metformin. The discovery of the fact that BCAA (Branched-chain Amino Acid) suppresses the side effects of metformin and increases hypoglycemic effect is considered to be very important for the future where metformin is expected to be used frequently.

The efficacy of diabetes mellitus drugs containing biguanide derivatives like metformin will be examined. According to our current knowledge, pancreas regains its activity after resting. Metformin lowers blood glucose by suppressing the manufacture of glucose in the liver, this allows the pancreas to rest without getting tired, and is considered to promote activation of the pancreas. Also, the hypoglycemic effect of metformin is remarkable when used in the early stage of diabetes mellitus. Addition of BCAA to metformin further enhances the hypoglycemic effect and the drug can also be administered without problems to older adults who require caution during administration.

Population aging is expected to progress throughout the world in the future, and elderly diabetic patients are also expected to increase. The number of patients with kidney failure undergoing hemodialysis will also increase leading to higher medical expenses. The composition for treating diabetes mellitus of the present invention with active components metformin and BCAA is expected to be good news not only for Japan but also for countries and people all over the world.

BRIEF DESCRIPTION OF THE DRAWINGS

FIG. 2 is a graph showing the relationship between drug administration and HBA1c and lactate levels for patients in Prescription Example 13.

Figure 1:
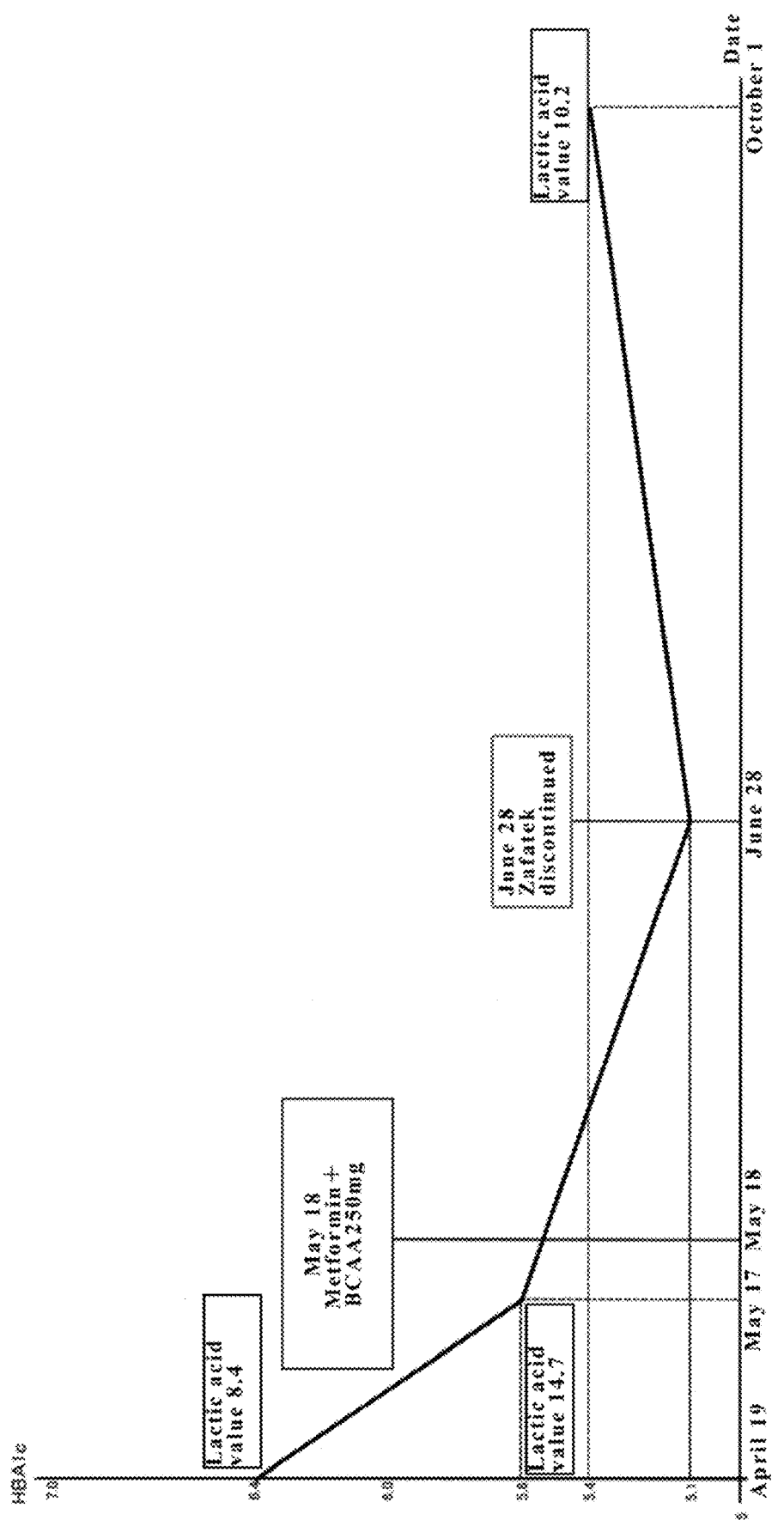
FIG. 1 is a graph showing the transition of HbA1c for a patient undergoing metformin+BCAA therapy when the new drug (DPP4 inhibitor: Zafatek) is used independently or in combination.

DETAILED DESCRIPTION OF THE INVENTION (Composition for Treating Diabetes Mellitus)

A preferred embodiment of the present invention will be described in detail. The composition for treating diabetes mellitus of the present invention with hypoglycemic effect that suppresses lactic acidosis without substantially increasing the blood lactate concentration, has a branched-chain amino acid or a derivative of a branched-chain amino acid, and biguanide derivative or a salt of the biguanide derivative as the active component.

The drug containing the composition of the present invention may be administered as a combination drug in which both the components are combined in one formulation or administered in the form of separate formulations. Administration as separate formulations includes simultaneous and separate administrations. Also, when administering separately, the compound of the present invention may be administered first, and the other drug may be administered later, or the other drug may be administered first, and the compound of the present invention may be administered later, and respective mode of administration may be the same or different.

Each component constituting the therapeutic agent for diabetes mellitus of the present invention will be described. First, the composition for treating diabetes mellitus of the present invention contains a branched-chain amino acid or a derivative of a branched-chain amino acid as one of the active components.

The form of branched-chain amino acids include but are not limited to pure crystalline amino acids in free form, and their salts, peptides, or derivatives. Branched-chain amino acid in the salt form include pharmacologically acceptable salt forms such as sodium, potassium, hydrochloride, and acetate salts. Branched-chain amino acid in the peptide form include peptides obtained by peptideization of branched-chain amino acid as a dipeptide or tripeptide. Peptideizing branched-chain amino acid in this way enables peptides to be effectively utilized after conversion into free amino acids by hydrolysis with the in vivo action of peptidase. Derivatives of branched-chain amino acids include N-acetyl-DL-leucine, DL-norleucine, N-acetyl-DL-isoleucine, 4-hydroxy-L-isoleucine, and β-methyl norleucine. These derivatives are converted to free amino acids by the in vivo effect of enzymes such as acylase and can be used effectively.

The composition for treating diabetes mellitus of the present invention may contain either leucine, isoleucine or valine, or both leucine and isoleucine, or, all of leucine, isoleucine, and valine as the branched-chain amino acid.

Leucine, isoleucine, and valine are compounds represented by the respective chemical formulas given below.

[Chemical formula 1]

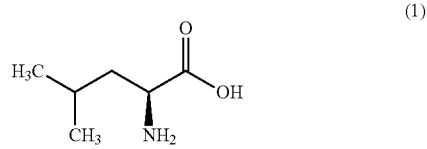

(1)

[Chemical formula 2]

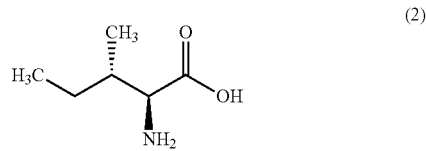

(2)

[Chemical formula 3]

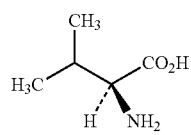

(3)

The composition for treating diabetes mellitus of the present invention may contain all of leucine, isoleucine, and valine as the branched-chain amino acid. When the composition for treating diabetes mellitus containing both leucine and isoleucine as branched-chain amino acids is specifically used as a preparation, then leucine, isoleucine, and valine will not have an antagonistic action on the albumin production effect of each other, and additive effectiveness of in vivo production promoting effect of albumin can be improved.

The composition for treating diabetes mellitus of the present invention may contain only one of leucine, isoleucine, or valine as the branched-chain amino acid. The composition for treating diabetes mellitus containing leucine, isoleucine, or valine independently will further decrease the in vivo load of proteins, effectively reducing side effects when the composition for treating diabetes mellitus is used as a preparation.

For example, if the emphasis is on the efficacy during administration of the composition for treating diabetes mellitus to patients with liver diseases, both leucine and isoleucine must be included in the composition for treating diabetes mellitus to improve the additive effect of the production promoting effect of albumin described above. On the other hand, if the emphasis is on the safety during administration of the composition for treating diabetes mellitus to patients with liver diseases, the composition for treating diabetes mellitus must include leucine or isoleucine to effectively reduce the side effects caused by the reduction of the protein load as described above. That is, the composition for treating diabetes mellitus can achieve a balance between efficacy and safety based on the condition of patients with liver diseases.

On the other hand, the composition for treating diabetes mellitus of the present invention contains a biguanide derivative or a salt of the biguanide derivative as one of the active components.

The salt of the biguanide derivative must be a pharmacologically acceptable salt, the salts include, for example, salts with inorganic acid, salts with organic acid, and salts with an acidic amino acid. The salts with inorganic acids include, for example, salts with hydrochloric acid, hydrobromic acid, nitric acid, sulfuric acid, and phosphoric acid. The salts with organic acids include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. The salts with acidic amino acid include, for example, salts with aspartic acid and glutamic acid.

Specifically, metformin hydrochloride, represented by the following chemical formula (4),

[Chemical formula 4]

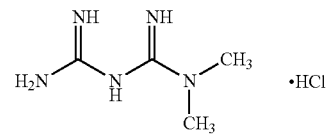

(4)

as a salt of the biguanide derivative can be included as one of the active components.

Also, biguanide derivatives buformin and phenformin are compounds represented by the following chemical formula [I] or [II], respectively.

[Chemical formula 5]

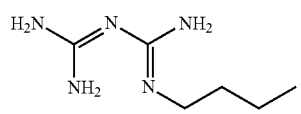

(5)

[Chemical formula 6]

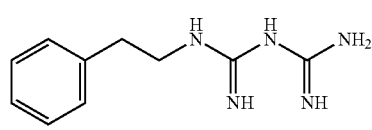

(6)

Moreover, pharmaceutically acceptable salts of buformin or phenformin can be used including salts with inorganic acids such as hydrochloric acid, hydrobromic acid, hydroiodic acid, nitric acid, sulfuric acid, phosphoric acid; salts with organic acids such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid, and sulfosalicylic acid; quaternary ammonium salt with methyl bromide, and methyl iodide; salts with halogen ions such as bromine ion, chlorine ion, and iodine ion; salts with alkali metals such as lithium, sodium, and potassium; salts with alkaline earth metals such as calcium, and magnesium; metal salts with iron and zinc; salt with ammonia; salts with organic amines such as triethylenediamine, 2-aminoethanol, 2,2'-Iminobis (ethanol), 1-deoxy-1-(methylamino)-2-D-sorbitol, 2-amino-2-(hydroxymethyl)-1,3-propanediol, procaine, and N,N'-bis(phenylmethyl)-1,2-ethanediamine, but hydrochloride is preferred. Moreover, buformin or phenformin may take the form of a hydrate or a solvate.

When geometric or optical isomers are present in buformin or phenformin, their isomers or salts are also included in the scope of the present invention. When proton tautomers exist in buformin or phenformin, their tautomers or salts are also included in the scope of the present invention.

When crystalline polymorph and crystalline polymorph group (crystalline polymorph system) exists in buformin and phenformin or their geometric isomers, optical isomers, proton tautomers or salts, then their crystalline polymorphs and crystalline polymorph groups (crystalline polymorph system) are also included in the scope of the present invention. Here, the crystalline polymorph group (crystalline polymorph system) refers to the individual crystals formed at each stage when the crystal form changes based on the conditions and state (including the state of the formulation) such as production, crystallization, preservation of these crystals, and the entire process.

The composition for treating diabetes mellitus of the present invention may contain the branched-chain amino acid or derivative of a branched-chain amino acid, and biguanide derivative or salt of the biguanide derivative as the active component, and the specific formulation may be prepared, for example, by mixing with excipients, binders, stabilizers, lubricants, flavoring agents, disintegrating agents, coating agents, coloring agents, buffering agents, aqueous solvents, oily solvents, tonicity agents, dispersants, preservatives, solubilizing agents, fluidizing agents, soothing agents, pH adjusting agents, antiseptics, and bases. Also, physiologically permissible carriers can be used as additive components of the composition for treating diabetes mellitus.

Excipients include sugars such as lactose, sucrose, glucose, D-mannitol, and sorbitol; cellulose such as crystalline cellulose, hydroxypropyl cellulose, hydroxypropyl methylcellulose, methylcellulose, and their derivatives; starch such as corn starch, potato starch, α-starch, dextrin, β-cyclodextrin, sodium carboxymethyl starch, hydroxypropyl starch, and their derivatives; silicates such as synthetic aluminum silicate, magnesium aluminosilicate, calcium silicate, and magnesium silicate; phosphates such as calcium phosphate, carbonates such as calcium carbonate; sulfates such as calcium sulfate; tartaric acid, potassium hydrogen tartrate, and magnesium hydroxide.

Binders include cellulose such as crystalline cellulose, hydroxypropyl cellulose, hydroxypropyl methylcellulose, methylcellulose and their derivatives; starch such as corn starch, potato starch, α-starch, dextrin, β-cyclodextrin, sodium carboxymethyl starch, hydroxypropyl starch, and their derivatives; sugars such as lactose, sucrose, glucose, D-mannitol, and sorbit; agar, stearyl alcohol, gelatin, tragacanth, polyvinyl alcohol, and polyvinylpyrrolidone.

Stabilizers include p-hydroxybenzoic esters such as methyl paraben and propyl paraben; alcohols such as chlorobutanol, benzyl alcohol, and phenylethyl alcohol; phenols such as phenol and cresol; sulfites such as sodium bisulfite and sodium sulfite; edetate salts such as disodium edetate, and tetrasodium edetate; hydrogenated oil, sesame oil, sodium chondroitin sulfate, dibutyl hydroxy toluene, adipic acid, ascorbic acid, L-ascorbyl stearate, sodium L-ascorbate, L-aspartic acid, monosodium L-aspartate, sodium acetyltryptophanate tryptophan, acetanilide, aprotinin solution, aminoethylsulfonic acid, aminoacetic acid, DL-alanine, L-alanine, benzalkonium chloride, and sorbic acid.

Lubricants include stearic acids such as stearic acid, calcium stearate, and magnesium stearate; waxes such as white beeswax and carnauba wax; sulfate such as sodium sulfate; silicates such as magnesium silicate and light anhydrous silicic acid; lauryl sulfate such as sodium lauryl sulfate; powdered acacia, cocoa butter, carmellose calcium, carmellose sodium, callopeptide, hydrated silicon dioxide, hydrated amorphous silicon oxide, dried aluminum hydroxide gel, glycerin, light liquid paraffin, crystalline cellulose, hydrogenated oil, synthetic aluminum silicate, sesame oil, wheat starch, talc, macrogols, and phosphoric acid.

Flavoring agents include sugars such as lactose, sucrose, glucose, and D-mannitol; ascorbic acid, L-aspartic acid, L-ascorbyl stearate, monosodium L-aspartate, magnesium L-aspartate, aspartame, sweet *hydrangea* leaf, sweet *hydrangea* leaf extract, powdered sweet *hydrangea* leaf, aminoethylsulfonic acid, aminoacetic acid, DL-alanine, sodium saccharin, DL-menthol, and l-menthol.

Disintegrating agents include cellulose such as crystalline cellulose, hydroxypropyl cellulose, hydroxypropyl methylcellulose, methylcellulose, and their derivatives; carbonates such as calcium carbonate, sodium bicarbonate, and magnesium carbonate; starch such as corn starch, potato starch, α-starch, dextrin, β-cyclodextrin, sodium carboxymethyl starch, hydroxypropyl starch, and their derivatives; agar, gelatin, tragacanth, adipic acid, alginic acid, and sodium alginate.

Coating agents include cellulose derivatives such as cellulose acetate, hydroxypropyl cellulose, cellulose acetate phthalate, and hydroxypropyl methylcellulose; shellac, polyvinylpyrrolidones, polyethylene glycol, macrogols, methacrylic acid copolymers, liquid paraffin, and eudragit. Coloring agents include indigo carmine, caramel, and riboflavin.

Buffering agents include aminoacetic acid, L-arginine, benzoic acid, sodium benzoate, ammonium chloride, potassium chloride, sodium chloride, dried sodium sulfite, dried sodium carbonate, diluted hydrochloric acid, citric acid, calcium citrate, sodium citrate, disodium citrate, calcium gluconate, L-glutamic acid, L-monosodium glutamate, creatinine, chlorobutanol, crystalline sodium dihydrogen phosphate, disodium succinate, acetic acid, potassium acetate, sodium acetate, tartaric acid, sodium bicarbonate, sodium carbonate, triethanolamine, lactic acid, sodium lactate solution, glacial acetic acid, boric acid, maleic acid, anhydrous sodium citrate, anhydrous sodium acetate, anhydrous sodium carbonate, anhydrous disodium hydrogen phosphate, anhydrous trisodium phosphate, anhydrous sodium dihydrogen phosphate, DL-malic acid, phosphoric acid, trisodium phosphate, sodium hydrogen phosphate, dipotassium phosphate, potassium dihydrogen phosphate, sodium dihydrogen phosphate, and sodium dihydrogen phosphate monohydrate.

Aqueous solvents include distilled water, physiological saline, and Ringer's solution. Oily solvents include vegetable oils such as olive oil, sesame oil, cottonseed oil, and corn oil; and propylene glycol. Tonicity agents include potassium chloride, sodium chloride, glycerin, sodium bromide, D-sorbitol, nicotinamide, glucose, and boric acid.

Dispersants include stearic acid and its salts such as zinc stearate and magnesium stearate; acacia, propylene glycol alginate, sorbitan sesquioleate, D-sorbitol, tragacanth, methylcellulose, aluminum monostearate, aminoalkyl methacrylate copolymer RS, lactose, concentrated glycerin, propylene glycol, macrogols, and sodium lauryl sulfate.

Preservatives include alcohols such as chlorobutanol, phenethyl alcohol, propylene glycol, and benzyl alcohol; p-hydroxybenzoic esters such as isobutyl parahydroxybenzoate, ethyl parahydroxybenzoate and methyl parahydroxybenzoate; benzalkonium chloride, benzethonium chloride, dried sodium sulfite, cresol, chlorocresol, dibutyl hydroxy toluene, potassium sorbate, sodium dehydroacetale, phenol, formalin, phosphoric acid, benzoin, thimerosal, thymol, and sodium dehydroacetate.

Solubilizing agents include sodium benzoate, ethylenediamine, citric acid, sodium citrate, glycerin, sodium acetate, sodium salicylate, sorbitan sesquioleate, nicotinamide, glucose, benzyl alcohol, polyvinylpyrrolidones, acetone, ethanol, isopropanol, D-sorbitol, sodium bicarbonate, sodium carbonate, lactose, urea, and sucrose.

Fluidizing agents include stearic acid and its salts such as calcium stearate and magnesium stearate; hydrated silicon dioxide, talc, anhydrous ethanol, crystalline cellulose, synthetic aluminum silicate, and calcium phosphate. Soothing agents include benzalkonium chloride, procaine hydrochloride, meprylcaine hydrochloride, lidocaine hydrochloride, and lidocaine.

pH adjusting agents include hydrochloric acid, citric acid, succinic acid, acetic acid, boric acid, maleic acid, and sodium hydroxide. Antiseptics include benzoic acid, sodium benzoate, cetylpyridinium chloride, salicylic acid, sodium salicylate, sorbic acid, potassium sorbate, thymol, methyl parahydroxybenzoate, and butyl parahydroxybenzoate.

Bases include vegetable oils such as olive oil, sesame oil, and wheat-germ oil; glycerin, stearyl alcohol, polyethylene glycols, propylene glycol, cetanol, lard, white petrolatum, paraffin, bentonite, isopropyl lanolate, Vaseline, polysorbates, macrogols, lauryl alcohol, sodium lauryl sulfate, ethyl linoleate, sodium hydrogen phosphate, and rosin.

There is no specific restriction on the dosage form of the composition for treating diabetes mellitus of the present invention, granules, powders, tablets, capsules, syrups, emulsions and suspensions are some of the different forms; some of the parenteral agents are injections such as subcutaneous injection, intravenous injection, intramuscular injection, and intraperitoneal injections; transdermal administration agents such as ointments, creams, and lotions; suppositories such as rectal and vaginal suppositories; nasal administration formulations. Various preparations mentioned above can be produced by known methods commonly used in the preparation process.

Next, the specific effect of the composition for treating diabetes mellitus of the present invention "Hypoglycemic effect without substantially increasing the blood lactate concentration" will be described.

In the present invention, "Hypoglycemic effect without substantially increasing the blood lactate concentration" indicates that when the composition for treating diabetes mellitus is administered and hypoglycemic fall rate is measured with oral glucose tolerance test and blood lactate concentration is measured, the increase rate of blood lactate concentration is 35% or less at the dose at which the hypoglycemic fall rate is 60 to 80%, while the preferable increase rate of blood lactate concentration is 30% or less at the dose at which the hypoglycemic fall rate is 60 to 80%, and increase rate of blood lactate concentration of 25% or less at the dose at which the hypoglycemic fall rate is 60 to 80% is further preferred. That is, for example, when hypoglycemic fall rate is measured with oral glucose tolerance test and blood lactate concentration is measured, blood lactate concentration is suppressed to 45 mg/dl or less even when the composition for treating diabetes mellitus is administered with a dose at which the hypoglycemic fall rate indicates 60 to 80% for diabetic patients with blood lactate concentration indicated to be between 4 to 33 mg before administration of the composition.

Next, diabetic patients who can be considered for administration of the composition for treating diabetes mellitus of the present invention will be described.

Since the composition for treating diabetes mellitus of the present invention has hypoglycemic effect without substantially increasing the blood lactate concentration as described above, the composition is effective especially for diabetic patients who are prone to develop lactic acidosis. Such diabetic patients who tend to develop lactic acidosis includes, for example, diabetic patients with a history of lactic acidosis, diabetic patients with renal dysfunction, diabetic patients with liver dysfunction, diabetic patients with cardiovascular disorders, diabetic patients with impaired pulmonary function, diabetic patients who are prone to hypoxemia, diabetic patients who consume excess alcohol, diabetic patients with gastrointestinal disorders, patients with type 2 diabetes, and elderly diabetic patients.

The composition for treating diabetes mellitus of the present invention is specifically effective for diabetic patients who tend to develop lactic acidosis as described above, and even among these patients, the composition for treating diabetes mellitus is suitable for administration to diabetic patients with renal dysfunction. Renal dysfunction includes chronic renal failure, diabetic nephropathy, glomerulonephritis, immune complex nephritis, acute renal failure, interstitial nephritis, nephrosclerosis, renal infarction, renal tubule dysfunction, renal impairment due to drugs, renal impairment due to pesticides, and uremia.

Next, the administration method of the composition for treating diabetes mellitus of the present invention will be described.

The administration method of the composition for treating diabetes mellitus of the present invention, for example, can be but are not limited to peroral or parenteral administration as a pharmaceutical composition (formulation) using branched-chain amino acid or derivatives of branched-chain amino acids, biguanide derivatives or salts of the biguanide derivatives and the above mentioned additive components.

The dosage of the composition for treating diabetes mellitus of the present invention can be appropriately determined based on the type of target (warm-blooded animals such as human beings), severity of symptoms, age, administration method, and results of diagnosis by doctors, but for example, the following administration dosages of biguanide derivatives are preferred for an adult, 0.1 to 2000 mg/kg per day in the case of oral administration, and 0.1 to 1000 mg/kg per day is preferred in the case of parenteral administration. The dosage given above is the value per unit weight (body weight of 1 kg) of the administration target. The dosage of the present invention mentioned above may be administered at once or divided into several doses over a period of 1 to 7 days depending on the severity of symptoms and diagnosis of the doctor.

(Form of the Preparations)

The composition for treating diabetes mellitus can be suitably used in the form of a preparation. The preparation forms include but are not limited to infusion preparations, oral preparations, transdermal absorption preparations, suppositories, patches, ointments, haps, and lotions.

The composition for treating diabetes mellitus can be suitably used in the form of infusion preparation. By preparing the composition for treating diabetes mellitus in the form of infusion preparation, the composition for treating diabetes mellitus can be administered quickly and effectively through the blood vessels, and maximum efficacy in promoting the in vivo albumin production can be demonstrated.

Infusion preparation types include injections and drip infusions. When the composition for treating diabetes mellitus is used as an injection or drip infusion, they should be sterilized and made isotonic with blood. When preparing the composition for treating diabetes mellitus as an injection or drip infusion, diluting agents that can be used for example include water, ethyl alcohol, polyethylene glycol, propylene glycol, ethoxylated isostearyl alcohol, polyoxylated isostearyl alcohol, and polyoxyethylene sorbitan fatty acid esters, and sufficient quantity of salt, glucose, or glycerin can be added to prepare a solution that is isotonic with body fluids. The infusion preparation can be cryopreserved, or can also be stored by removing moisture by lyophilization. The infusion preparation that has been stored after lyophilization can be dissolved by adding distilled water for injections or sterilized water when required to be used.

The composition for treating diabetes mellitus can be suitably used in the form of oral preparations. By preparing the composition for treating diabetes mellitus in the form of oral preparations, the composition for treating diabetes mellitus can be administered easily and conveniently without invasion into the living organism, and adequate effect in promoting the in vivo albumin production can be demonstrated.

The oral preparations include but are not limited to tablets, powders, granules, fine granules, pills, capsules, lozenges, chewables, and syrups. When used as tablets, various carriers known in the field of hypoalbuminemia improvement can be used. Carriers include excipients such as lactose, sucrose, sodium chloride, glucose, urea, starch, calcium carbonate, kaolin, crystalline cellulose, and silicic acid; Binders such as water, ethanol, propanol, simple syrup, glucose solution, starch solution, gelatin solution, carboxymethylcellulose, shellac, methylcellulose, potassium phosphate, and polyvinylpyrrolidone; disintegrating agents such as dry starch, sodium alginate, powdered agar, laminaran powder, sodium bicarbonate, calcium carbonate, polyoxyethylene sorbitan fatty acid esters, sodium lauryl sulfate, stearic acid monoglyceride, starch, and lactose; Disintegrating inhibitors such as sucrose, stearin, cocoa butter, and hydrogenated oil; Absorption enhancers such as quaternary ammonium base, and sodium lauryl sulfate; moisturizers such as glycerin, and starch; Adsorbents such as starch, lactose, kaolin, bentonite, and colloidal silicic acid; Lubricants such as purified talc, stearate, boric acid powder, and polyethylene glycol. Such tablets may include, as necessary, tablets with a normal coating, sugar-coated tablets, gelatin-coated tablets, enteric coated tablets, film-coated tablets, double-layered tablets, and multi-layered tablets.

When used as a pill, various carriers known in the field of hypoalbuminemia improvement are used. Carriers include excipients such as glucose, lactose, starch, cocoa butter, hydrogenated vegetable oil, kaolin, and talc; Binders such as powdered acacia, tragacanth powder, gelatin, and ethanol; Laminaran, and agar.

The above mentioned oral preparation may further contain additives. Such additives include surfactants, absorption enhancers, fillers, bulking agents, moisturizers, antiseptics, stabilizers, emulsifiers, solubilizers, and salts for regulating osmotic pressure, and can be used by selecting based on the form for administration unit of the oral preparation.

The composition for treating diabetes mellitus of the present invention is not limited to the above embodiment. When the form of the composition for treating diabetes mellitus of the present invention is in the form of an oral preparation, a paste (thickeners, and gelling agents) may be added as necessary to prepare the composition in the form of a gel or as jelly. By adjusting the composition for treating diabetes mellitus of the present invention in the form of a gel or as jelly, oral administration becomes easy and absorption in the gastrointestinal tract also improves. The type of pastes include but are not limited to agar, gelatin, carrageenan, Arabic gum, guar gum, locust bean gum, tara gum, gellan gum, curdlan, xanthan gum, pullulan, pectin, sodium alginate, carboxymethylcellulose, other polysaccharides that can be usually used as a paste, and one or two or more types of these can be used in combination. The proportion of such types of paste should preferably be not more than five parts by mass for 100 parts by mass of the composition for treating diabetes mellitus that is prepared in the form of a gel or as jelly.

(Therapeutic Agents Used in the Treatment of Diabetes Mellitus Such as DPP4 Inhibitors)

The composition for treating diabetes mellitus of the present invention described above is also effective as an agent for treating, preventing and improving diseases and symptoms mediated by DPP4.

1. Supplementation and enhancement of the treatment and preventive effectiveness of the composition,
2. Improvement of the dynamics and absorption of the composition, reduction in dosage, and
3. May be administered as a drug combined with other drugs to alleviate side effects caused by the composition. For example, can be administered as a drug in combination with Branched-chain Amino Acids (BCAA), biguanide derivatives such as metformin or salts of the biguanide derivatives and derivatives of branched-chain amino acids or therapeutic agents used in the treatment of diabetes mellitus.

The above-mentioned therapeutic agents used in the treatment of diabetes mellitus include but are not limited to dipeptidyl peptidase-4 inhibitor (hereinafter abbreviated as "DPP4 inhibitor"), sulfonylurea drugs, biguanides, α-glucosidase inhibitors, insulin secretagogues, insulin sensitizers, insulin preparations, PPAR agonists (PPARα agonists, PPARγ agonists, PPARα+γ agonists, and PPAR pan agonists), β3 adrenergic receptor agonists, aldose reductase inhibitors, AMP kinase activator, 11β-hydroxysteroid dehydrogenase (11β-HSD1) type 1 inhibitor, lipase inhibitors, and appetite suppressants.

The drug containing the composition of the present invention may be administered as a combination drug in which both the components are combined in one formulation or administered in the form of separate formulations. Administration as separate formulations includes simultaneous and separate administrations. Also, when administering separately, the compound of the present invention may be administered first, and the other drug may be administered later, or the other drug may be administered first, and the compound of the present invention may be administered later, and respective mode of administration may be the same or different. The diseases for which therapeutic and prophylactic effect is obtained with the combination drug include but are not limited to any disease that supplements and enhances the therapeutic and preventive effect of the compound of the present invention.

DPP4 inhibitors include LAF-237, sitagliptin phosphate (MK-431, ONO-5435), BMS-477118, P93-01, GSK823093, GSK815541, GSK825964, TS-021, T-6666, SYR-322, E-3024, NN-7201, and PSN-9301.

Sulfonylurea drugs include acetohexamide, glibenclamide, gliclazide, glyclopyramide, chlorpropamide, tolazamide, tolbutamide, and glimepiride.

Biguanide drugs include buformin hydrochloride and metformin hydrochloride.

α-glucosidase inhibitors include acarbose, voglibose, and miglitol.

Insulin secretagogues include nateglinide, repaglinide, and mitiglinide. Insulin sensitizers include ONO-5816, YM-440, JTT-501, and NN-2344.

PPAR agonists include bezafibrate, clofibrate, fenofibrate, and gemfibrate that are PPAR α agonists, pioglitazone, troglitazone, and rosiglitazone that are PPAR γ agonists, muraglitazar, tesaglitazar, and ONO-5129 that are PPAR α+γ agonists, and GSK 677954, PLX 204, and MCC-555 that are PPAR pan agonists.

β3 adrenergic receptor agonists include AJ9677, L750355, and CP331648.

Aldose reductase inhibitors include epalrestat, fidarestat, and zenarestat.

An example of a lipase inhibitor is orlistat.

Appetite suppressants include cannabinoid receptor 1 antagonists (for example, rimonabant), melanin-concentrating hormone receptor antagonists (for example, GSK856464, ATC-0065, ATC-0175, and AMG-076), monoamine oxidase inhibitors (For example, mazindol and sibutramine), serotonin 2c receptor agonists (for example, APD-356, and SCA-136), histamine 3 receptor antagonists (for example, ABT-239, ABT-837, GT-2331, and NNC-0038-0000-1202), mazindol, and sibutramine.

DPP4 is a dipeptidyl peptidase IV that is also called DPP-IV, DP4, DPPIV, and CD26; this dipeptidyl peptidase IV is a serine protease that produces dipeptide Xaa-Pro or Xaa-Ala from a peptide chain having proline or alanine at the second position from the N end. DPP4 is widely distributed in mammalian tissues and is known to be present in kidney, liver, intestinal epithelium, placenta, and blood plasma, and is involved in the metabolism of various biologically active peptides. Among them, the powerful ability of DPP4 to promote insulin secretion and play the role as an enzyme for inactivating in vivo Glucagon-Like Peptide-1 (hereinafter abbreviated as GLP-1) that is responsible for regulating postprandial blood glucose has attracted attention.

In the same way as GLP-1, Gastric Inhibitory Polypeptide or Glucose-dependent Insulinotropic Peptide (referred to as GIP), Pituitary Adenylate Cyclase Activating Polypeptide (referred to as PACAP), and Vasoactive Intestinal Polypeptide; (referred to as VIP) are biologically active peptides that promote insulin secretion from the pancreas. DPP4 is also involved in the degradation of these biologically active peptides due to which compounds that inhibit DPP4 also suppresses degradation of these biologically active peptides, enhances action and insulin secretion, and is expected to be useful in prevention and treatment of diabetes mellitus (especially type 2 diabetes and the like) or in prevention and improving postprandial hyperglycemia, and impaired glucose tolerance.

DPP4 is also involved in the metabolism of neuropeptides such as neuropeptide Y, endomorphin 1, endomorphin 2, and substance P. Therefore, compounds that inhibit DPP4 can also be expected to be used as therapeutic agents or analgesics for schizophrenia, depression, anxiety, epilepsy, and stress-related diseases as they suppress the degradation of biologically active peptides.

DPP4 is known to be involved in the metabolism of various cytokines and chemokines, activation of T cells which are immunocompetent cells, adhesion of cancer cells to the endothelium, and proliferation of blood cells. Since compounds inhibiting DPP4 also inhibit these actions, they are useful for the treatment and prevention of autoimmune diseases such as rheumatoid arthritis and type I diabetes, allergic diseases such as asthma and food allergies, cancer, cancer metastasis, HIV infection, anemia, and thrombocytopenia.

Since high expression of DPP4 is found in skin fibroblasts of patients with psoriasis, rheumatoid arthritis and lichen planus, and high DPP4 activity is found in patients with prostatic hyperplasia, compounds that inhibit DPP4 are also expected to be effective in treating and preventing skin diseases (psoriasis, and lichen planus) and prostatic hyperplasia.

In addition to the above, compounds inhibiting DPP4 are also considered to be useful in treating and preventing hyperlipidemia, metabolic syndrome (syndrome X), diabetic complications, arteriosclerosis, polycystic ovary syndrome, infertility, growth disorders, arthritis, transplant rejection, enteritis, and trauma.

[Example of Execution]

The present invention will be described in detail with a formulation example, but the present invention is not intended to be limited to this formulation example alone. In the following examples, the drug to be administered is prescribed using the method for analyzing diabetes of the present invention.

That is, the following steps are performed.

(1) Step to measure HbA1c and lactate levels in patients (2) Step of blending a composition containing a branched chain amino acid and a biguanide derivative as active ingredients according to the measurement results of HbA1c and lactic acid levels (3) Step to measure changes in HbA1c and lactate levels after administration of the composition to the patient, (4) Step of repeating administration while adjusting the composition of the composition according to the measurement result after administration, and (5) Step of observing the correlation between the process until the HbA1c or lactic acid level reaches the reference value and the formulation of the composition at each administration.

In addition, the following steps are performed, depending on the situation.

(1) Step to measure HbA1c and lactate levels in a patient and detect tumor markers in the patient, (2) Step of blending a composition containing a branched chain amino acid, a biguanide derivative and an antidiabetic agent as active ingredients according to the measurement results of HbA1c and lactic acid levels, (3) Step of measuring changes in HbA1c, lactate levels and tumor markers after administration of the composition to the patient, (4) Step of repeating administration while adjusting the composition of the composition according to the measurement result after administration, and (5) Step of observing the correlation between the process until the HbA1c or lactic acid level reaches the reference value and the formulation of the composition at each administration.

In the prescription examples below, along with providing treatment based on the administration of metformin hydrochloride and branched-chain amino acids such as L-isoleucine, L-leucine, and L-valine (hereinafter referred to as "Metformin+BCAA therapy"), a general therapeutic agent used in the treatment of diabetes mellitus such as DPP4 inhibitor is used in combination, depending on the condition of the patient. For each prescription example, the glycemic status of the patient that is dependent on the administered active components and the component amount is measured using HbA1c (glycated hemoglobin) along with changes in the lactic acid value, and opinion of the doctor is recorded together with the change in the values.

Prescription Example 1

TABLE 1

| Component type | Active component name | Dosage | Administration interval | Observation period |
|---|---|---|---|---|
| Biguanide derivatives etc. Branched-chain amino acids etc. | Metformin hydrochloride L-Isoleucine L-Leucine L-valine | 125 mg/administration 952 mg/administration 1904 mg/administration 1144 mg/administration | 1 time/day | 1 month |

| | | | | |
|---|---|---|---|---|
| Gender | Female | | | |
| Age | 99 years | | | |
| Prescription period | Jun. 13, 2015 | HbA1c | 6.6 mg/dl | |
| | Jul. 18, 2015 | HbA1c | 5.6 mg/dl | Lactic acid value 8.1 |
| | Jul. 29, 2015 | HbA1c | 5.5 mg/dl | |
| | Aug. 17, 2015 | | | Lactic acid value 15.9 |
| | Sept. 4, 2015 | | | Lactic acid value 12.1 |
| | Sept. 5, 2015 | HbA1c | 5.1 mg/dl | |
| | Nov. 5, 2015 | | | Lactic acid value 17.2 |

Opinion of the Doctor

The patient was an older adult and was suffering from renal dysfunction, but HbA1c level dropped by 1.0 (approximately 15%) in around one month, the patient regained appetite with the decrease in blood glucose level, and there were no side effects. The lactic acid value at the end of the observation period also stabilized to a normal value at 8.1 (<16.0).

In the United States, Cr is a measure of renal dysfunction, and use of metformin is prohibited in men who have a Cr of 1.5 or more and women who have a Cr of 1.4 or more because the possibility for lactic acid values to increase is high (There are no special regulations in Japan).

In this prescription example, a 99-year-old female patient was provided treatment for about 5.5 months from Jun. 13, 2015, to Nov. 29, 2015. During her first visit, HbA1c was 6.6, and she was diagnosed with renal anemia. On June 27, Hb was 5.5 and Ht was 17.3.

Metformin hydrochloride 250 mg was prescribed on Jun. 15, 2015. Cr was 1.67 on Jul. 29, 2015. BCAA2P was added on Jul. 30, 2015. On Aug. 17, 2015, the lactic acid value was 15.9. Since HbA1c level dropped to 5.1 on Sep. 5, 2015, the dose of metformin was reduced from 250 mg to 125 mg.

On Nov. 9, 2015, the HbA1c level was 5.2, the lactic acid value was 20.9 and Cr was 1.65, but the administration of metformin was discontinued on Nov. 18, 2015. The values recorded were the last as the patient died on November 29. Anemia due to impaired function of bone marrow and renal impairment associated with anemia are the main ailments of senility. The cause of death was not lactic acidosis due to metformin. Lactic acidosis can be considered as the cause of death if the lactic acid value exceeds 40.

Another example is of a 97-year-old female patient who had little consciousness when she was brought to me, and the lactic acid value was 41.9 on Jul. 2, 2016, she gradually regained consciousness about a month later, on Aug. 9, 2016, the lactic acid value returned to a normal value 7.3, and she could understand when others spoke to her (she used to take deep breaths during stethoscope examination, and stick her tongue out). Though there is a 2-year age difference between the patients who are 99 and 97 years old, this case serves as a reference to the fact that even if the lactic acid value exceeds 41, lactic acidosis does not become a direct cause of death.

The result of this prescription example is that metformin can be used in combination with BCAA even at the advanced age of 99 when Cr is more than 1.4, and renal failure is so severe that transfusion or use of renal hormone (erythropoietin) is inevitable. Even the patient who died did not require dialysis.

Prescription Example 2

Metformin was used in combination with BCAA (Branched-chain Amino Acid) to treat a diabetic patient who was using insulin since the age of 17.

TABLE 2

| Component type | Active component name | Dosage | Administration interval | Observation period |
|---|---|---|---|---|
| Biguanide derivatives etc. Branched-chain amino acids etc. | Metformin hydrochloride L-Isoleucine L-Leucine L-valine | 250 mg/administration 952 mg/administration 1904 mg/administration 1144 mg/administration | 3 times/day | 1 month |

| | | |
|---|---|---|
| Gender | Female | |
| Age | 41 years | |
| Prescription period | Aug. 12, 2015 | Lactic acid value 5.9 |
| | Aug. 26, 2015 | Lactic acid value 4.7 |
| | Sep. 12, 2015 | Lactic acid value 3.6 |

Opinion of the Doctor

Although blood glucose level did not decrease, the lactic acid value dropped from 5.9 to 3.6.

Prescription Example 3

The patient was not able to eat meals after having become bedridden and was administered high-calorie infusion, following this the blood glucose level gradually increased. One tablet of metformin (250 mg) and BCAA for hypoalbuminemia was prescribed.

TABLE 3

| Component type | Active component name | Dosage | Administration interval | Observation period |
|---|---|---|---|---|
| Biguanide derivatives etc. Branched-chain amino acids etc. | Metformin hydrochloride L-Isoleucine L-Leucine L-valine | 125 mg/administration 952 mg/administration 1904 mg/administration 1144 mg/administration | 1 day | 1 month |

| | |
|---|---|
| Gender | Female |
| Age | 89 years |
| Prescription period | Jul. 7, 2015  HbA1c 6.2 mg/dl |
| | Aug. 5, 2015  HbA1c 5.7 mg/dl  Lactic acid value 10.8 |

Opinion of the Doctor

HbA1c level had decreased by 0.5 mg/dl (about 8%) in one month, and metformin was set at 125 mg/day as the level sometimes dropped too low during this period. Bringing borderline diabetes mellitus to the normal value range is relatively difficult, but the lactic acid value also reached the normal range (<16.0) without side effects, even though the patient was an older adult.

Prescription Example 4

Metformin (250 mg)×1 to 2 tablets were prescribed in combination with insulin treatment for a patient was bedridden due to hypoxic encephalopathy resulting from hypoglycemia.

TABLE 4

| Component type | Active component name | Dosage | Administration interval | Observation period |
|---|---|---|---|---|
| Biguanide derivatives etc. Branched-chain amino acids etc. | Metformin hydrochloride L-Isoleucine L-Leucine L-valine | 250 mg/administration 952 mg/administration 1904 mg/administration 1144 mg/administration | 2 times/day | 13 months |

| | |
|---|---|
| Gender | Male |
| Age | 68 years |
| Prescription period | Oct. 29, 2013  HbA1c 7.6 mg/dl |
| | Mar. 16, 2014  HbA1c 5.9 mg/dl (Reference value 6.2) |
| | Jun. 6, 2015   HbA1c 5.9 mg/dl  Lactic acid value 5.1 |

Opinion of the Doctor

The HbA1c level which was 7.6 mg/dl during first prescription decreased to 5.9 mg/dl (approximately 20%) and the latest lactic acid value during the observation period was stable at 5.1 (<16.0), a normal value.

Prescription Example 5

TABLE 5

| Component type | Active component name | Dosage | Administration interval | Observation period |
|---|---|---|---|---|
| Biguanide derivatives etc. Branched-chain amino acids etc. | Metformin hydrochloride L-Isoleucine L-Leucine L-valine | 250 mg/administration 952 mg/administration 1904 mg/administration 1144 mg/administration | 3 times/day | 6 months |

| | |
|---|---|
| Gender | Male |
| Age | 49 years |
| Prescription period | Mar. 13, 2014  HbA1c 9.2 mg/dl |
| | Dec. 8, 2014   HbA1c 11.1 mg/dl  Lactic acid value 16.3 |
| | Mar. 18, 2015  HbA1c 8.6 mg/dl |
| | Apr. 1, 2015   HbA1c 8.2 mg/dl  Lactic acid value 9.3 |
| | Jun. 12, 2015  HbA1c 7.4 mg/dl  Lactic acid value 12.3 |

Opinion of the Doctor

HbA1c value decreased from 8.6 mg/dl to 7.4 mg/dl (approximately 14%) in 2 months from the beginning of 2015 when BCAA and metformin (250 mg)×6 tablets were given in combination with insulin treatment, and the HbA1c value was approximately 30% lower than the maximum value of 11.1 mg/dl. Lactic acid value also stabilized at 12.3, a normal value.

Prescription Example 6

Metformin and BCAA was prescribed for the treatment of diabetes mellitus.

TABLE 6

| Component type | Active component name | Dosage | Administration interval | Observation period |
|---|---|---|---|---|
| Biguanide derivatives etc. Branched-chain amino acids etc. | Metformin hydrochloride L-Isoleucine L-Leucine L-valine | 250 mg/administration 952 mg/administration 1904 mg/administration 1144 mg/administration | 2 times/day | 16 months |

| | |
|---|---|
| Gender | Female |
| Age | 74 years |
| Prescription period | Mar. 27, 2014  HbA1c 9.4 mg/dl |
| | Jul. 10, 2014  HbA1c 6.1 mg/dl |
| | Mar. 28, 2015  Lactic acid value 6.1 |
| | Jun. 6, 2015   HbA1c 5.6 mg/dl |

Opinion of the Doctor

In the initial stage, HbA1c level decreased from 9.4 mg/dl to 6.1 mg/dl (approximately 35%) in a brief period from March to July 2014, and in a period of one year and few months including the above period, HbA1c level decreased by approximately 40%, from 9.4 mg/dl to 5.6 mg/dl. As of June 2015, lactic acid value also stabilized at a normal value of 9.6 (<16.0).

Prescription Example 7

TABLE 7

| Component type | Active component name | Dosage | Administration interval | Observation period |
|---|---|---|---|---|
| Biguanide derivatives etc. | Metformin hydrochloride | 250 mg/administration | 1 time/day | 1 month |
| Branched-chain amino acids etc. | L-Isoleucine L-Leucine L-valine | 952 mg/administration 1904 mg/administration 1144 mg/administration | | |

| | | | |
|---|---|---|---|
| Gender | Male | | |
| Age | 76 years | | |
| Prescription period | Sep. 11, 2015 | HbA1c 7.0 mg/dl | |
| | Oct. 4, 2015 | HbA1c 6.3 mg/dl | |
| | Oct. 16, 2015 | | Lactic acid value 14.2 |

Opinion of the Doctor

In the initial stage, the HbA1c level decreased from 7.0 mg/dl to 6.3 mg/dl (approximately 10%) in a brief period from September to October 2015, and in October 2015 lactic acid value was also stable at 14.2 (<16.0).

Prescription Example 8

TABLE 8

| Component type | Active component name | Dosage | Administration interval | Observation period |
|---|---|---|---|---|
| Biguanide derivatives etc. | Metformin hydrochloride | 250 mg/administration | 2 times/day | 9 months |
| Branched-chain amino acids etc. | L-Isoleucine L-Leucine L-valine | 952 mg/administration 1904 mg/administration 1144 mg/administration | | |

| | | | |
|---|---|---|---|
| Gender | Male | | |
| Age | 75 years (diabetes mellitus, dementia) | | |
| Prescription period | Oct. 14, 2015 | HbA1c 8.6 mg/dl | Lactic acid value 18.6 |
| | Jun. 29, 2016 | HbA1c 7.9 mg/dl | |
| | Jul. 4, 2016 | | Lactic acid value 15.1 |

Opinion of the Doctor

HbA1c level was 8.6 and lactic acid value was 18.6>16.0 from the test results during the first visit (Oct. 14, 2015) of the patient and was administered oral antidiabetic drugs (5 types, one of which was 500 mg of metformin) along with administration of insulin (5 units) for 24 hours.

The patient was in a state where glycemic control was not possible. The uric acid value was 18.6 (>Standard value 16) indicating that the dose of metformin could not be increased any further. Metformin (+BCAA also) was increased for treatment of the patient. Diarrhea, the second side effect of metformin set in and administration of drugs to stop diarrhea did not yield any results. However, diarrhea could be stopped by significantly reducing the lipid intake and this is a measure for the second side effect of metformin.

The efficacy of metformin, a drug for diabetes mellitus will be discussed According to our knowledge, pancreas regains its activity after resting. Metformin lowers blood glucose by suppressing the manufacture of glucose in the liver, this allows the pancreas to rest and is considered to promote activation of the pancreas. Also, the hypoglycemic effect of metformin is remarkable when used in the early stage of diabetes mellitus. Addition of BCAA to metformin further enhances the hypoglycemic effect and can also be administered without problems to older adults who require caution during administration.

Population aging is expected to progress throughout the world in the future, and elderly diabetic patients are also expected to increase. The number of patients with kidney failure undergoing hemodialysis will also increase leading to higher medical expenses. Both metformin and BCAA of the present invention are expected to be good news not only for Japan but also for countries and people all over the world.

Glycemic control of the patient in this example was almost successful under the following conditions. I am saying "Almost successful" because stabilizing HbA1c level to a lower value is possible, but the function of the pancreas was considered to have declined due to aging, and bringing the HbA1c level below the standard value of 6.2 was likely to be difficult.

Thus, a little more time is required to stabilize blood glucose levels of patients for whom glycemic control is not possible (especially older adults). Approximately eight months was required to reach the following state. For this reason, administration of the composition for treating diabetes mellitus of the present invention which contains both metformin and BCAA as the active components must be started at an early stage of diabetes. This patient had started to develop necrosis of the left leg because of the above therapy, but at present, the symptoms cannot be observed at all.

HbA1c level for this patient on Jun. 29, 2016, was 7.9 and lactic acid value on Jul. 4, 2016, was 15.1. The patient was administered with metformin 1000 mg, pioglitazone (was taking from the first visit) an oral drug that does not burden the pancreas, and 5 to 8 units of insulin with effect lasting for 24 hours.

This patient was referred to our hospital by a different hospital, and the patient exercised in a wheelchair underwent rehabilitation for dementia and was on a 1600 kcal/day diet. Since dementia had advanced, and the patient was bedridden during our initial examination, we reduced the diet to 1200 kcal/day. This difference of 400 kcal can be the energy that is almost equal or higher to the exercise done by the patient in the wheelchair.

Prescription Example 9

TABLE 9

| Component type | Active component name | Dosage | Administration interval | Observation period |
|---|---|---|---|---|
| Biguanide derivatives etc. | Metformin hydrochloride | 250 mg/administration | 2 times/day | 4 months |
| Branched-chain amino acids etc. | L-Isoleucine L-Leucine L-valine | 952 mg/administration 1904 mg/administration 1144 mg/administration | | |

| | |
|---|---|
| Gender | Male |
| Age | 52 years |
| Prescription period | Feb. 24, 2016 HbA1c 9.1 mg/dl |
| | Jun. 25, 2016 HbA1c 7.6 mg/dl |

Opinion of the Doctor

This case with improvement of not only HbA1c but also the liver enzyme that is involved in fatty liver (non-alcoholic) was added to the results of metformin+BCAA therapy of the composition for treating diabetes mellitus of the present invention.

Prescription Example 10

TABLE 10

| Component type | Active component name | Dosage | Administration interval | Observation period |
|---|---|---|---|---|
| Biguanide derivatives etc. | Metformin hydrochloride | 250 mg/administration | 2 times/day | 11 months |
| Branched-chain amino acids etc. | L-Isoleucine L-Leucine L-valine | 952 mg/administration 1904 mg/administration 1144 mg/administration | | |

| | | | |
|---|---|---|---|
| Gender | Male | | |
| Age | 73 years | | |
| Prescription period | Jun. 11, 2015 | HbA1c . . . 6.4 mg/dl | |
| | Aug. 5, 2015 | | Lactic acid value 9.5 |
| | Feb. 5, 2016 | HbA1c . . . 5.5 mg/dl | |
| | Jul. 5, 2016 | HbA1c . . . 5.5 mg/dl | Lactic acid value 15.1 |

Opinion of the Doctor

The treatment of diabetes mellitus is considered to require exercise therapy. Exercising the body to control blood glucose certainly brings down the blood glucose level.

The patient of this prescription example was already bedridden with little consciousness during the first visit. During the first visit (March 2015), he was suffering from hypoglycemia during the treatment of diabetes mellitus, developed hypoxic encephalopathy and was bedridden. He was feed 1100 kcal/day through a feeding tube. Since the patient suffered from aspiration pneumonia that was because of reflux from the stomach for about six months, he was fed using IVH (1000 kcal high-calorie infusion through the jugular vein) from September up to July 2016. Only drugs are being passed to the stomach through the nasal passage, and the patient has settled down. Medicine is drugs and metformin 500 mg+BCAA.

The values shown in the above table are,

| | |
|---|---|
| June 2015 | HbA1c 6.4 (metformin 250 mg, lactic acid value 9.5) |
| July 2016 | HbA1c 5.5 (lactic acid value 15.1) |

The results indicate that the composition for treating diabetes mellitus of the present invention can be used for glycemic control of a person who was not able to move his body for a year and few months after the first visit. The results also indicate that blood glucose can be controlled even though glucose was directly injected into the blood vessels with IVH procedure. A better way to control the blood glucose level is providing metformin+BCAA therapy with the composition for treating diabetes mellitus of the present invention while the diabetes mellitus condition is still not serious.

Prescription Example 11

TABLE 11

| Component type | Active component name | Dosage | Administration interval | Observation period |
|---|---|---|---|---|
| Biguanide derivatives etc. | Metformin hydrochloride | 250 mg/administration | 1 time/day (other, increased dose to 3 times/day) | 4 months |
| Branched-chain amino acids etc. | L-Isoleucine L-Leucine L-valine | 952 mg/administration 1904 mg/administration 1144 mg/administration | | |
| Diabetes mellitus therapy (DPP4 inhibitor) | Dipeptidyl peptidase-4 inhibitor | 100 mg/administration | 1 time/week | 1 month |

| | | | |
|---|---|---|---|
| Gender | Male | | |
| Age | 85 years | | |
| Prescription period | Apr. 19, 2016 | HbA1c 6.4 mg/dl | Lactic acid value 8.4 |
| | May 17, 2016 | HbA1c 5.6 mg/dl | Lactic acid value 14.7 |
| | Jun. 28, 2016 | HbA1c 5.1 mg/dl | Lactic acid value 12.2 |
| | Jul. 20, 2016 | HbA1c 5.2 mg/dl | |
| | Aug. 24, 2016 | | Lactic acid value 13.3 |
| | Oct. 1, 2016 | HbA1c 5.4 mg/dl | Lactic acid value 10.2 |

Opinion of the Doctor

FIG. 1 shows the change in values of HbA1c for a patient undergoing metformin+BCAA therapy when the new drug (DPP4 inhibitor: Zafatek), a therapeutic agent for the treatment of diabetes mellitus is used independently or in combination. For this patient, HbA1c was 5.6 with only the new drug (DPP4 inhibitor) but was noticed only when administration of metformin 250 mg+BCAA was started. Glycemic control was not good with postprandial blood glucose at 246 mg/dl on May 9, 2016, and metformin+BCAA was started on May 18, 2016. HbA1c dropped to 5.1 on Jun. 28, 2016, and the new drug was discontinued. The treatment was changed to just metformin+BCAA therapy. On Jul. 20, 2016, HbA1c increased by 0.1 to 5.2. The patient did not have a good appetite at the beginning of hospitalization, but as on July 20, he was able to eat all meals. Glycemic control had also improved (fasting blood glucose, and postprandial blood glucose)

One of the side effects of metformin is elevated lactic acid values, but there is data to suggest that the new drug also has the same side effect. This suggests that BCAA must be used even in combination with the new drug.

HbA1c was 6.4, and the lactic acid value was 8.4 for this patient during admission (Apr. 19, 2016), and HbA1c was 5.6, and the lactic acid value was 14.7 on May 17, 2016. Administration of metformin was started from May 18, 2016. The lactic acid value was 13.3 on Aug. 24, 2016, HbA1c was 5.4 on Oct. 1, 2016, and an equivalent effect was observed even with the new drug.

Prescription Example 12

TABLE 12

| Component type | Active component name | Dosage | Administration interval | Observation period |
|---|---|---|---|---|
| Biguanide derivatives etc. | Metformin hydro-chloride | 250 mg/administration | 1 times/day | 3 months |
| Branched-chain amino acids etc. | L-Isoleucine L-Leucine L-valine | 952 mg/administration 1904 mg/administration 1144 mg/administration | | |

| Gender | Female | | | |
|---|---|---|---|---|
| Age | 89 years | | | |
| Prescription period | Jul. 21, 2016 | HbA1c . . . 6.9 mg/dl | | |
| | Aug. 3, 2016 | HbA1c . . . 6.9 mg/dl | | |
| | Aug. 24, 2016 | | Lactic acid value 8.4 | |
| | Sep. 1, 2016 | HbA1c . . . 6.9 mg/dl | | |
| | Oct. 1, 2016 | HbA1c . . . 6.4 mg/dl | Lactic acid value 9.1 | |

Opinion of the Doctor

This prescription example is of a case in which the side effects were suppressed by careful administration of the drug. During first visit (Jul. 21, 2016), HbA1c was 6.9, and the lactic acid value was 17.9. A slightly higher dose 4 mg of antihypertensive diuretic fluitran that is administered with care to diabetic patients was used, but fluitran worsened the condition of diabetes mellitus and another antihypertensive drug was administered, and the condition of the patient was monitored.

One tablet of metformin (250 mg) and BCAA was administered on Jul. 25, 2016, the lactic acid value was 8.4 on Aug. 24, 2016, and HbA1c was 6.4 on Oct. 1, 2016.

The results indicated that the lactic acid value could be reduced significantly, but mean blood glucose level could not be reduced. Significant reduction in the lactic acid value was considered to have prevented the condition of diabetes mellitus from worsening. In future, HbA1c was expected to come down by reducing or not using fluitran and adding metformin to the treatment. The dosage of fluitran was gradually reduced and replaced by another antihypertensive drug on Sep. 27, 2016.

There were significant changes in the lactic acid values when measured repeatedly, and we came to understand that the value increases when the patient is not feeling well (such as infectious disease, anemia, fatigue, increase in GOTGPT, and elevated BUN) from the monitoring of the patient for about two years. If the lactic acid value increases during the course of treating diabetes mellitus with metformin+BCAA based on the composition for treating diabetes mellitus of the present invention, factors other than the dosage of metformin have to be considered.

Prescription Example 13

Reference FIG. 2 shows the relation between the medicine applied to a patient and the values of HBA1c and lactate. Only three months after the combination of the branched-chain amino acids (BCAA)(leucine, isoleucine, and valine) and metformin was applied (February, 2017), the values of HBA1c and lactate were clearly and significantly reduced. As shown in Table 13, various combinations of the medicine were applied experimentally to the same patient from 2000. However, the value of HBA1c was never reduced below 0.68. Just after the combination of the present invention was applied on February 2017, the values of HBA1c and lactate were significantly improved.

TABLE 13

| Date | Name of medicine | Amount | Note |
|---|---|---|---|
| August 2000 | Amaryl (1 mg) | | |
| September 2001 | | | |
| February 2002 | Amaryl (1 mg) | 3T | |
| February 2003 | Amaryl (1 mg) | 1T | |
| Oct. 2006 | Amaryl (1 mg) | 2T | Increased |
| | ACTOS (15) | 1T | |
| January 2010 | JANUVIA (50) | 1T | Changed |
| | Amaryl (1 mg) | 1T | |
| Mar. 2010 | JANUVIA (50) | 1T | Increased |
| | Amaryl (1 mg) | 2T | |
| September 2010 | ACTOS (30) | 1T | Because blood glucose is increased |
| | Amaryl (1 mg) | 2T | Increased |
| October 2010 | ACTOS (30) | 1T | |
| | Amaryl (1 mg) | 3T | |
| January 2011 | GLACTIV (25) | 1T | |
| | ACTOS | 1T | |
| | Glimepiride (1) | 3T | |
| April 2011 | JANUVIA (50) | 1T | |
| | Pioglitazone (30) | 1T | |
| | Glimepiride (1) | 3T | |
| May 2013 | JANUVIA (50) | 1T | |
| | METGLUCO (250) | 2T | Metformin was first used |
| | Voglibose (0.2) | 2T | |
| September 2013 | JANUVIA (75) | 1T | |
| | Pioglitazone (15) | 1T | |
| | METGLUCO (250) | 2T × 2 | |
| | Voglibose (0.2) | 2T × 2 | |
| June 2014 | ONGLYZA (5) | 1T | |
| | Pioglitazone (15) | 1T | |
| | METGLUCO (250) | 2T × 2 | |
| | Voglibose (0.2) | 2T × 2 | |
| September 2014 | ONGLYZA (5) | 1T | |
| | Pioglitazone (15) | 1T | |
| | METGLUCO (250) | 3T | |
| | Voglibose (0.2) | 2T × 2 | |

TABLE 13-continued

| Date | Name of medicine | Amount | Note |
|---|---|---|---|
| June 2016 | ONGLYZA (5) | 1T | |
| | Pioglitazone (15) | 1T | |
| | METGLUCO (250) | 4T | |
| | Voglibose (0.2) | 2T × 2 | |

Prescription Example 14

Figure 3:
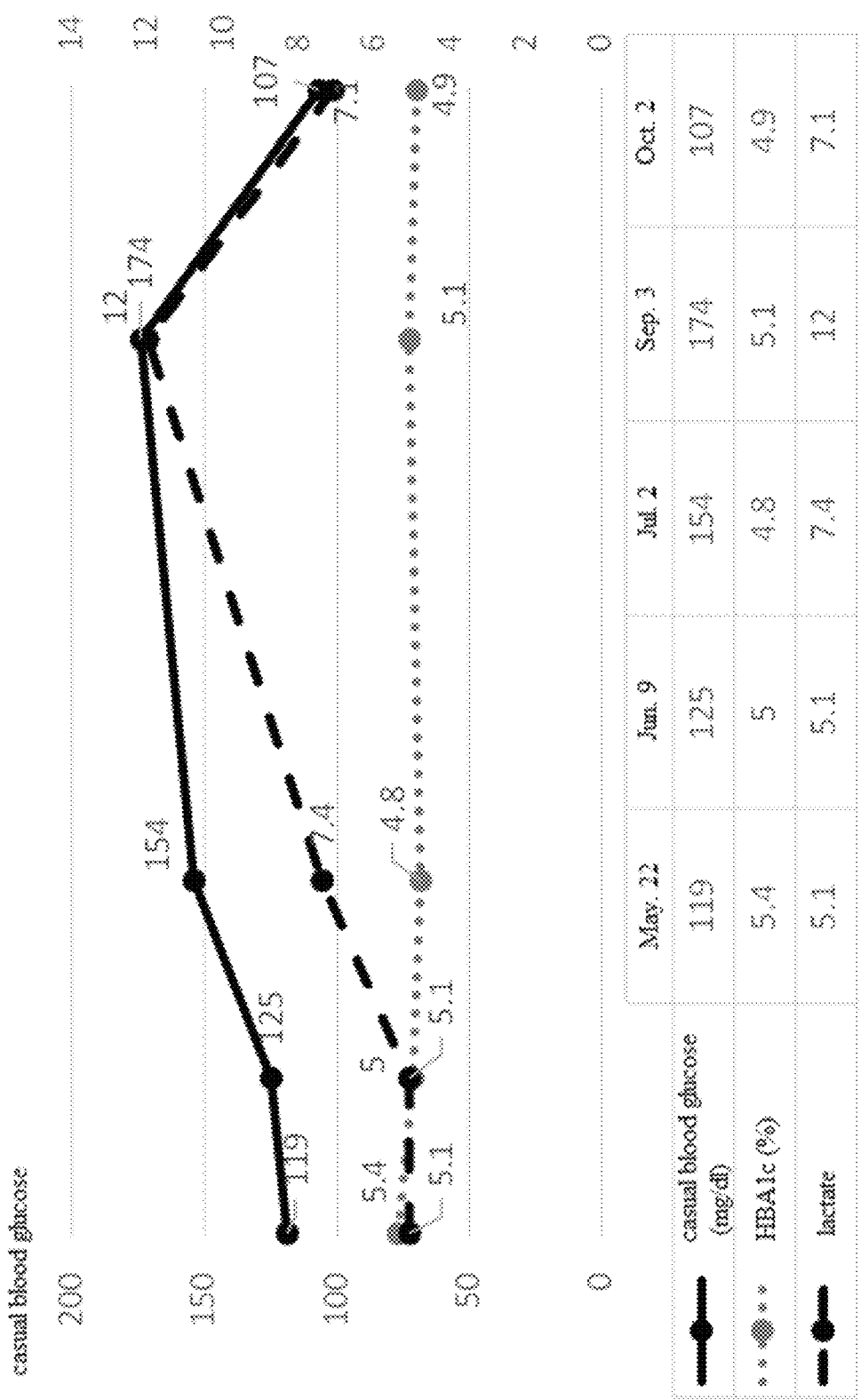
FIG. 3 is a graph showing changes in blood glucose level, HbA1c, and lactated milk with respect to the patient of Prescription Example 14.

Furthermore, Reference FIG. 3 shows the relation between the medicine applied to another patient and the values of HBA1c casual blood glucose and lactate. From May 22, 2018 to Sep. 3, 2018, glimepiride (4 mg) and JANUVIA (100 mg) were combined with BCAA and applied to the patient. During the above described period, the values of the blood glucose and lactate remained at a high level. However, after the combination of BCAA (leucine, isoleucine, and valine) and metformin was applied (October, 2018), the values of HBA1c and lactate were clearly and significantly reduced on that month.

JANUVIA was applied before the metformin hydrochloride was applied. JANUVIA is a sitagliptin phosphate hydrate used as a therapeutic agent of diabetes for blocking an enzyme that decomposes incretin since the incretin functions to keep the blood glucose constant. When the blood glucose is high, JANUVIA is applied to enhance insulin secretion-promoting action and glucagon concentration-lowering action for improving the blood glucose control.

As understood from Reference FIG. 3 and Table 14, the effect of reducing lactate in addition to HBA1c and blood glucose cannot be obtained only by merely combining anti-diabetic agents with BCAA (leucine, isoleucine, and valine).

TABLE 14

| Date | HBA1c (%) | casual blood glucose (mg/dl) | lactate | name of medicine |
|---|---|---|---|---|
| May 22 | 5.4 | 119 | 5.1 | Glimepiride (4 mg) + JANUVIA (100 mg) + BCAA (1P) |
| June 9 | 5 | 125 | 5.1 | Glimepiride (4 mg) + JANUVIA (100 mg) + BCAA (1P) |
| June 9 | 4.8 | 154 | 7.4 | Glimepiride (4 mg) + JANUVIA (100 mg) + BCAA (1P) |
| September 3 | 5.1 | 174 | 12 | Glimepiride (4 mg) + JANUVIA (50 mg) + BCAA (2P) |
| October 2 | 4.9 | 107 | 7.1 | Glimepiride (4 mg) + Metformin (250 mg) + BCAA (2P) |

As explained above, the combination and composition of the metformin hydrochloride and the branched-chain amino acids described in the claims have an advantage over the other combinations.

(Predominancy of the Metformin)

Furthermore, since the biguanide derivatives other than the metformin tend to produce a cancer, it is meaningless to combine the biguanide derivatives other than the metformin with BCAA.

1) Biguanide Derivatives

Among approximately 40 kinds of currently used treating agents of diabetes mellitus, the agents having the effect of increasing the value of lactate are only the biguanide derivatives (metformin) and rapid-acting insulin secretion promoters (GLUFAST, Starsis, FASTIC). In the rapid-acting insulin secretion promoters, Starsis, FASTIC are same (hereafter, referred to as nateglinide). Thus, rapid-acting insulin secretion promoters are substantially two kinds.

Although the metformin may cause lactic acidosis, GLUFAST and the nateglinide do not cause lactic acidosis (confirmed by manufacturers).

Accordingly, the risk of causing lactic acidosis arises only when the metformin is used. Namely, it is meaningless to combine the biguanide derivatives other than the metformin with BCAA which has the effect of reducing the value of lactate.

2) Characteristics of Metformin and Branched-Chain Amino Acids (1) Metformin

Gluconeogenesis in the liver is suppressed without stimulating the pancreas (without promoting the secretion of insulin). In addition, the value of the blood glucose is reduced by promoting the consumption of the lactate in the muscle. The most negative side effect is to increase the value of lactate.

(2) BCAA (Branched-Chain Amino Acids)

It is currently found that BCAA can be ingredients of the muscle and have the effect of reducing the value of lactate. From the above described characteristics (1) (2), it can be understood that the metformin is suitably combined with BCAA. Furthermore, the following data shows the possibility of reducing the risk of the cancer by independently using BCAA or simultaneously using BCAA and the metformin.

Among 40 or more patients of the diabetes mellitus treated by the inventor of the present invention, the combination of BCAA and the metformin was used for all patients except for one particular patient. Among the above described patients, only the particular patient got a cancer after two years treatment. In addition, it can be understood that the combination of BCAA and the metformin had the effect of reducing the value of the blood glucose without increasing the amount of the insulin. On the other hand, it is widely known that the insulin itself may increase the risk of the cancer and many cancer patients can be found in the patients of the diabetes mellitus. From the above described facts, the combination of BCAA and the metformin should be the first choice for the diabetes mellitus treatment.

3) Case of Lowering the Tumor Marker by Independently Using BCAA

Case (1) 88 year old, female

| Date | CEA | CA19-9 (sugar chain antigen) |
|---|---|---|
| Jun. 21, 2018 | 5.2 | 60 |
| Feb. 14, 2019 | 4.3 | 60 |

Case (2) 84 year old, male

| Date | CEA | CA19-9 (sugar chain antigen) |
|---|---|---|
| Dec. 18, 2018 | 4.8 | 75 |
| Feb. 1, 2019 | 3.7 | 68 |
| Apr. 1, 2019 | 3.8 | 57 |

Both CEA and CA19-9 are the tumor markers typically used. The standard value of CEA is 5 or less. The standard value of CA19-9 is 37 or less.

4) Case of Lowering the Tumor Marker by Simultaneously Using BCAA and Metformin

Case (3) 69 year old, female

| Date | CEA | CA19-9 (sugar chain antigen) |
| --- | --- | --- |
| Mar. 22, 2018 | 19.1 | 115 |
| Apr. 2, 2018 | 12.6 | 76 |

Case (4) 67 year old, female

| Date | CEA | CA19-9 (sugar chain antigen) |
| --- | --- | --- |
| Jun. 1, 2016 | 2.6 | 7.7 |
| May 3, 2017 | 10.4 | 12 |
| Aug. 2, 2017 | 7.4 | 10 |
| May 3, 2018 | 5.3 | 9 |
| Feb. 1, 2019 | 4.9 | 7 |

Case (5) 85 year old, male

| Date | CEA | CA19-9 (sugar chain antigen) |
| --- | --- | --- |
| Feb. 25, 2019 | 8.6 | 72 |
| Apr. 1, 2019 | 8.2 | 60 |

Case (6) 81 year old, female

| Date | CEA | CA19-9 (sugar chain antigen) |
| --- | --- | --- |
| Dec. 22, 2018 | 7.3 | — |
| Feb. 15, 2019 | 12.6 | 13 |
| Apr. 1, 2019 | 5.2 | 13 |

Case (7) 79 year old, male

| Date | CEA | CA19-9 (sugar chain antigen) |
| --- | --- | --- |
| Dec. 26, 2018 | 4.9 | 247 |
| Jan. 5, 2019 | 5.1 | 90 |
| Feb. 4, 2019 | 4.5 | 33 |
| Apr. 2, 2019 | 5.1 | 29 |

5) Case of Cancer Patient

From January 2019 to April 2019 (four months), the inventor of the present invention surveyed the patients who developed a cancer during the diabetes mellitus treatment. All the patients who developed the cancer used DPP-4 inhibitors. One of them used the combination of BCAA and the metformin first, but then started to use the DPP-4 inhibitor additionally. One month after started to use the DPP-4 inhibitor, a rectal cancer was developed. Other patients did not use the metformin. The above described patient having a rectal cancer also developed a peritoneal cancer and told by the doctor not to have much time left.

Hereafter, all cases of the survey during four months are listed below. Case (8) S. K., 77 year old, male, February 2018

The diabetes mellitus was treated by Trazenta (DPP-4 inhibitor) and GLUFAST.

A kidney cancer and a vesical cancer were developed.

Case (9) C. H., 89 year old, female

Trazenta was used until October 2018. Then, Trazenta was stopped to start dialysis treatment. A vesical cancer was developed on March 2019.

Case (10) S. O., 85 year old, male

The diabetes mellitus was treated from about 65 year old. During the treatment using Equa (DPP-4 inhibitor), a bowel cancer was developed.

Case (11) M. N., 82 year old, male

The diabetes mellitus was treated by Trazenta (5 mg).

A liver cancer was developed and found on March 2019.

Case (12) M., 82 year old, female

The diabetes mellitus was treated by JANUVIA (DPP-4 inhibitor) and BCAA (Amaryl).

A kidney cancer was found at the beginning of 2019, and the surgery was operated on March 2019.

Case (13) A. H., 80 year old, female

The diabetes mellitus was treated by JANUVIA from 2017.

A bone cancer was found on January 2019.

Case (14) N., male

The intractable diabetes mellitus was treated by using metformin, then started to use Equa (DPP-4 inhibitor) additionally. Six months after started to use Equa, a rectal cancer was developed.

Case (15) T. T., 74 year old, male

He was an intractable dialysis patient and the diabetes mellitus was treated by using TENELIA until October 2017. A lung cancer was developed on April 2019.

As a result, although the research was within a short term (about four month), all patients who recently developed the cancer used DPP-4 inhibitor. Almost all patients were around 80 year old. It is not certain why the doctor didn't use metformin and whether or not DPP-4 inhibitor increases the risk of cancer. However, since the combination of BCAA and the metformin can be easily applied even to the aged patients, the combination of BCAA and the metformin should be the first choice for the diabetes mellitus treatment.

6) Additional Case

BCAA was used for the patient of 82 year old. However, since the tumor marker became gradually higher, the metformin was additionally used. Consequently, CEA was rapidly reduced as shown in the table below.

Case (16) 82 year old, male

| Date | CEA | CA19-9 (sugar chain antigen) |
| --- | --- | --- |
| Aug. 1, 2018 | 6.2 | 50 |
| Nov. 1, 2018 | 6.9 | 43 |
| Feb. 1, 2019 | 6.2 | 101 |
| Apr. 8, 2019 | 10.4 | 60 |
| Apr. 20, 2019 | 7.6 | 89 |
| May 7, 2019 | 6.8 | 106 |
| Jun. 6, 2019 | 6.2 | 39 |

Figure 4:
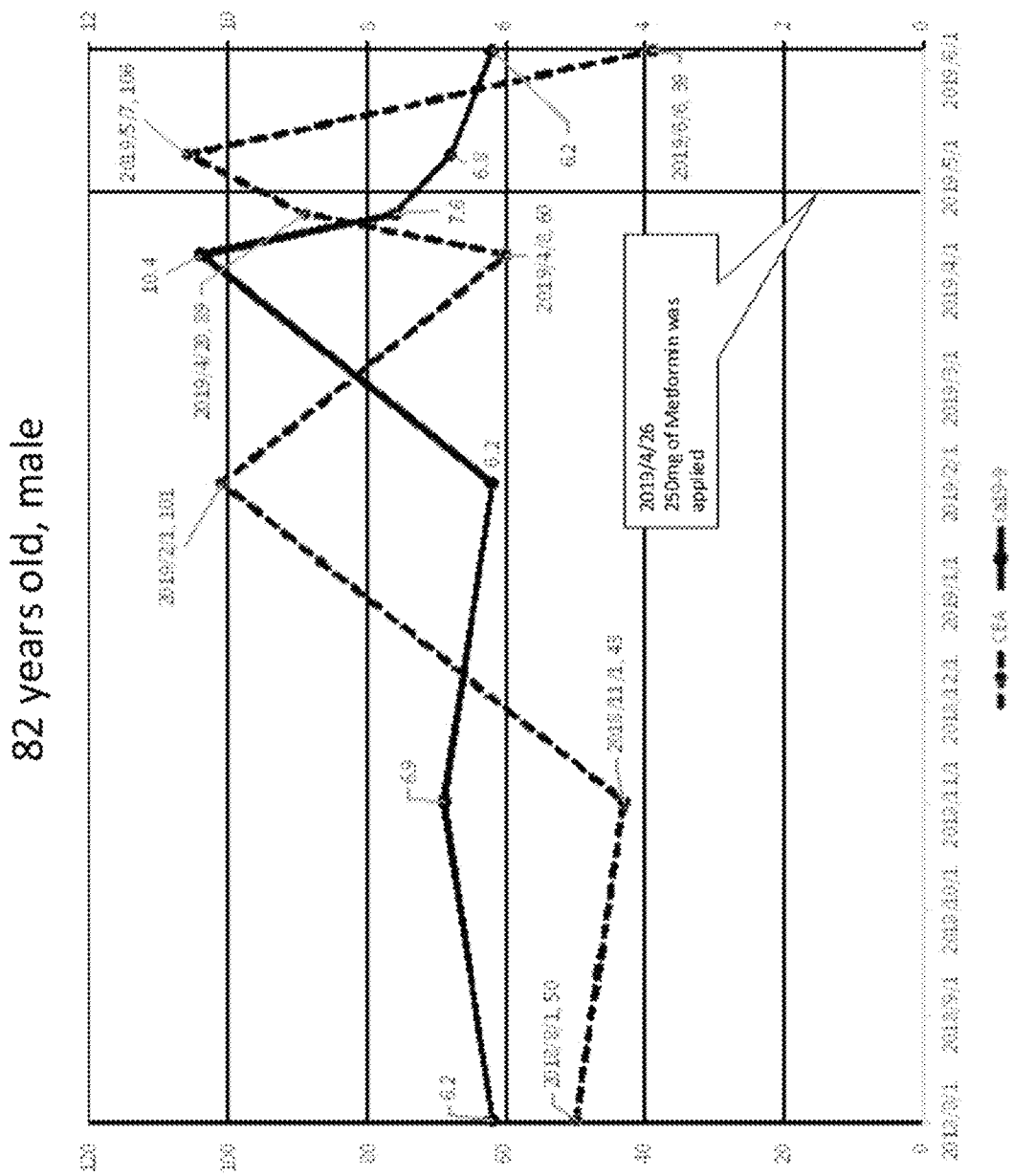
FIG. 4 is a graph showing changes in CEA related to "Case (16) 82 year old male".

As explained above, as shown in FIG. 4, the biguanide derivatives other than the metformin tend to produce a cancer, and the risk of the cancer can be reduced for the patients of the diabetes mellitus by combining the metformin. Accordingly, the combination of the metformin hydrochloride and the branched-chain amino acids recited in claim 1 of the present invention has unexpected properties compared to the generic combination of anti-diabetic agents and BCAA.

Case (17) M. S. 70 year old, male

This patient has been treated for diabetes only with DPP-4 inhibitors since 2011, and in April 2019, he suffered from gastric cancer and colorectal cancer and underwent surgery.

The patient has stopped using DPP-4 inhibitors since June 2019 and has been treating diabetes with "metformin+BCAA". He returned to work in April 2020 with good progress.

Case (18) F. A. 89 year old, female

The patient began treatment for diabetes with "metformin+BCAA" in 2015, but from 2016 she began treatment with only a DPP-4 inhibitor, at her own request. She had mandibular gingival cancer in January 2019 and underwent surgery. As of April 2020, this patient is receiving analgesic treatment. She hasn't taken BCAAs lately. Metformin is used to treat this patient's diabetes, but as of April 27, HbA1c is 5.3 due to her loss of appetite and significant weight loss.

Thus, comparing Cases 17 and 18, in Case 18, the use of "metformin+BCAA" was discontinued and the treatment was changed to treatment with only a DPP-4 inhibitor. In case 18, use of metformin was subsequently resumed, but her recovery was slow.

As a result, it can be seen that the treatment of "metformin+BCAA" is superior because the course of case 17 in which the treatment using "metformin+BCAA" is continuously performed is better.

| Case (19) 77 year old, male | |
| --- | --- |
| 1997 | Laryngeal cancer |
| 2001 | Rectal cancer |
| 2009 | Diabetes → Treated with Tenelia (DPP-4 inhibitor) |
| 2017 | Hemodialysis started (October 2) |
| Oct. 23, 2017 | Start taking BCAA |
| Nov. 22, 2017 | Canceled Tenelia |

There is no significant increase in his blood sugar. It may also be due to a loss of appetite due to a precancerous condition.

| | |
| --- | --- |
| March 2019 | BCAA was discontinued due to high dose |
| April 2019 | Lung cancer found and radiation therapy implemented |
| May 2019 | Started taking metformin 250 mg after HD (hemodialysis). |

Since the lactic acid level usually decreases after HD, it was judged that taking metformin 250 mg was not a problem.

April 2020 It was confirmed by PET and MRI that the reduction of lung cancer was maintained and there was no metastasis. As of August 2020, this patient continues to take metformin 250 mg after HD. He has an appetite and is well and goes to the hospital. His blood sugar level is also stable.

The following conclusions were drawn from all the cases mentioned above.

(1) Metformin is not contraindicated for dialysis patients
(2) Metformin should be the first choice for diabetics
(3) BCAAs should be used positively especially for people with low albumin
(4) When using DPP-4 inhibitor, it should be used in combination with metformin.
(5) The single use of DPP-4 inhibitor is likely to lead to carcinogenesis.
(6) Both BCAA and metformin have anticancer effects and are highly likely to be effective in the radical treatment of cancer.
(7) Since type II diabetes is inherited, cancer may develop first in young people even if they do not have diabetes, and "metformin+BCAA" treatment prevents this. There is a possibility.

Therefore, "metformin+BCAA" has an action of lowering the blood glucose level without substantially raising the blood lactate level, and can also be expected to have an effect of suppressing cancer. From these facts, "metformin+BCAA" is the most suitable combination as a composition for treating diabetes.

Further, according to the present invention, by observing the process of numerical change until the HbA1c or lactic acid level reaches the reference value, the tendency of the tumor marker, and the correlation between the composition at the time of each administration, the diabetes You can know the medical condition. Thereby, according to the present invention, it is possible to perform a follow-up analysis of diabetes while reducing the burden on the patient and the risk of carcinogenicity due to lactic acidosis.

INDUSTRIAL APPLICABILITY

As described above, according to the therapeutic agent for the treatment of diabetes mellitus of the present invention, a therapeutic agent with excellent hypoglycemic effect that suppresses lactic acidosis without substantially increasing the blood lactate concentration and at the same time can prevent the initiation of lactic acidosis can be provided. A therapeutic agent that can prevent and treat hyperglycemia without increasing the blood lactate concentration which may cause lactic acidosis can be provided to diabetic patients according to the present invention.

What is claimed is:

1. A method of determining a composition effective for treating diabetes, the method, comprising:
    a step to measure HbA1c and lactate levels in blood of a patient,
    a step of blending components of a branched chain amino acid and a biguanide derivative as active ingredients according to the measurement results of HbA1c and lactate levels; to form the composition,
    a step to measure changes in HbA1c and lactate levels after administration of the composition to the patient,
    a step of repeating administration while adjusting the components of the composition according to the measurement result after administration, and
    a step of observing the correlation between the measurement results of the HbA1c and lactate levels and the components of the composition at each administration until one of the HbA1c and lactate levels reaches a reference value.

2. A method of determining a composition effective for treating diabetes, the method comprising:
    a step to measure HbA1c and lactate levels in blood of a patient and detect tumor markers in the patient,
    a step of blending components of a branched chain amino acid, a biguanide derivative and an antidiabetic agent as active ingredients according to the measurement results of HbA1c and lactate levels; to form the composition,
    a step of measuring changes in HbA1c, lactate levels and tumor markers after administration of the composition to the patient,
    a step of repeating administration while adjusting the components of the composition according to the measurement result after administration, and
    a step of observing the correlation between the measurement results of the HbA1c and lactate levels and the components of the composition at each administration until one of the HbA1c and lactate levels reaches a reference value.

3. The method of determining the composition effective for treating diabetes according to the claim 1, wherein leucine, isoleucine, and valine is included as the branched-chain amino acid.

4. The method of determining the composition effective for treating diabetes according to the claim 2, wherein leucine, isoleucine, and valine is included as the branched-chain amino acid.

5. The method of determining the composition effective for treating diabetes according to claim 1, wherein metformin hydrochloride is included as the biguanide derivative.

6. The method of determining the composition effective for treating diabetes according to claim 2, wherein metformin hydrochloride is included as the biguanide derivative.

* * * * *